(12) United States Patent
Ollivier

(10) Patent No.: US 8,942,827 B2
(45) Date of Patent: Jan. 27, 2015

(54) MULTIZONE EPICARDIAL PACING LEAD

(71) Applicant: Sorin CRM S.A.S., Clamart Cedex (FR)

(72) Inventor: Jean-Francois Ollivier, Villiers-le-Bacle (FR)

(73) Assignee: Sorin CRM SAS, Clamart (FR)

( * ) Notice: Subject to any disclaimer, the term of this patent is extended or adjusted under 35 U.S.C. 154(b) by 165 days.

(21) Appl. No.: 13/630,482

(22) Filed: Sep. 28, 2012

(65) Prior Publication Data

US 2013/0325095 A1    Dec. 5, 2013

(30) Foreign Application Priority Data

Sep. 30, 2011    (FR) .................................. 11 58882

(51) Int. Cl.
*A61N 1/00*    (2006.01)
(52) U.S. Cl.
USPC .......................................................... 607/119
(58) Field of Classification Search
USPC .......... 607/115, 116, 142, 119, 126, 129, 130
See application file for complete search history.

(56) References Cited

U.S. PATENT DOCUMENTS

| 2007/0043412 | A1 | 2/2007 | Janssens et al. | |
| 2008/0046062 | A1* | 2/2008 | Camps et al. ............... | 607/133 |
| 2008/0177343 | A1 | 7/2008 | Dal Molin et al. | |
| 2009/0157136 | A1 | 6/2009 | Yang et al. | |
| 2009/0192572 | A1 | 7/2009 | Dal Molin et al. | |

FOREIGN PATENT DOCUMENTS

| EP | 1938861 A1 | 7/2008 |
| EP | 2082684 A1 | 7/2009 |
| WO | WO 2005/039690 A1 | 5/2005 |

OTHER PUBLICATIONS

Foreign Search Report (Annexe Au Rapport De Recherche Preliminaire Relatif A La Demande De Brevet Francais No. FR 1158882 FA 755954), Apr. 18, 2012.
CryoLife, BioGlue® Surgical Adhesive, http://cryolife.com/products/bioglue-surgical-adhesive.

* cited by examiner

*Primary Examiner* — Scott Getzow
(74) *Attorney, Agent, or Firm* — Foley & Lardner LLP

(57) ABSTRACT

A multizone epicardial pacing lead (10) having a lead body (12) with a proximal connector (14) for coupling to a generator of an active implantable medical device and, distally, an anchor to an epicardium wall and an active part comprising a plurality of stimulation electrodes, coming into contact with, or penetrating, the epicardium wall. This active part comprises a distributor housing (16) and a network of flexible microcables (18) radiating from the housing. Each microcable is formed of an electrically insulated conductor comprising at least one denuded area (20), each of these areas forming a stimulation electrode.

24 Claims, 4 Drawing Sheets

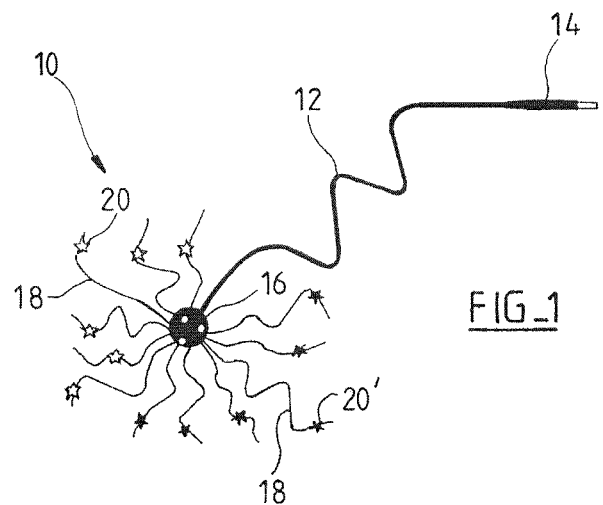
FIG_1
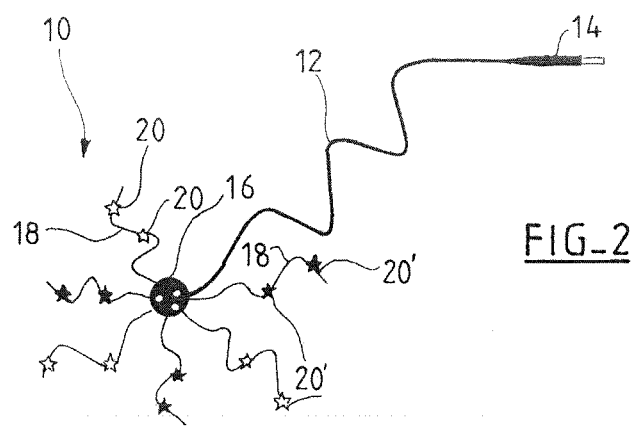
FIG_2
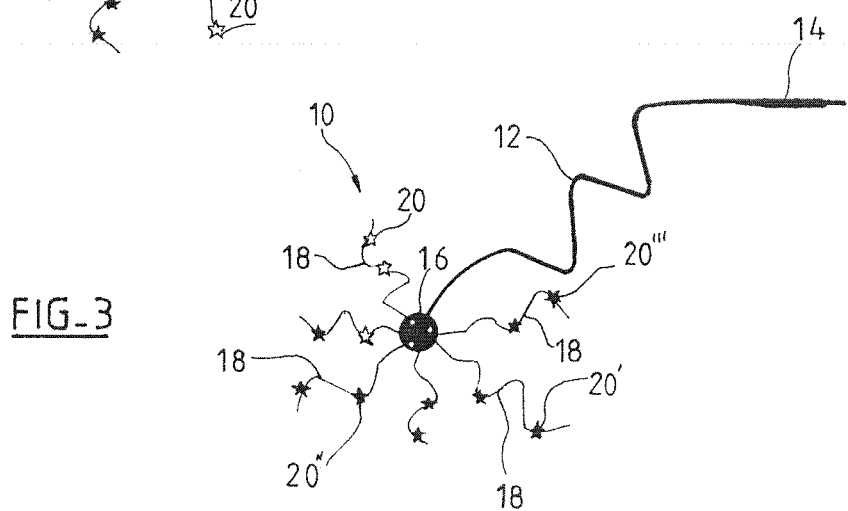
FIG_3

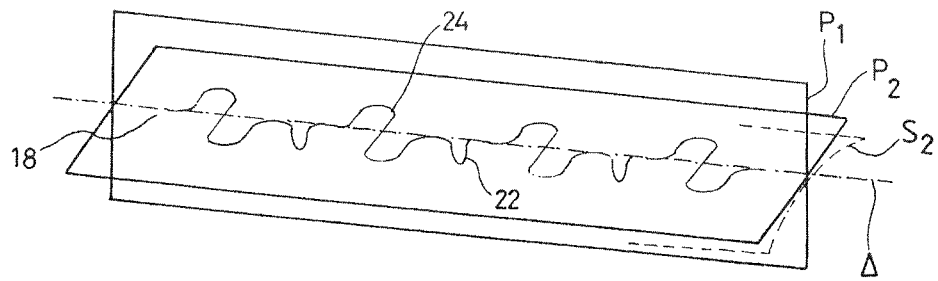
FIG_4
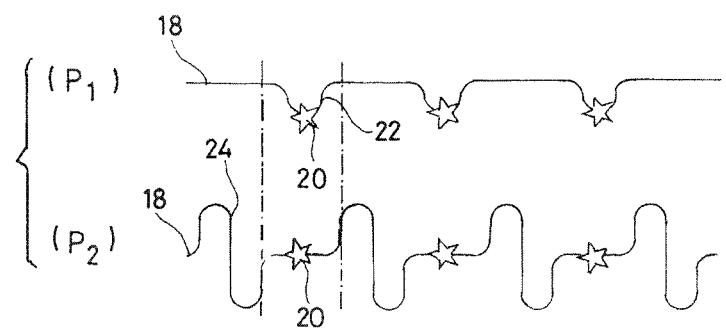
FIG_5
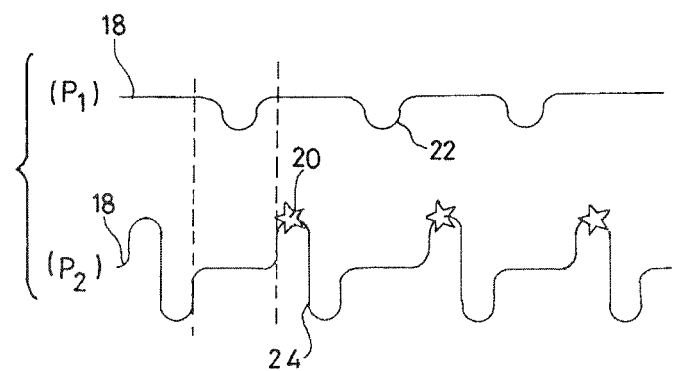
FIG_6

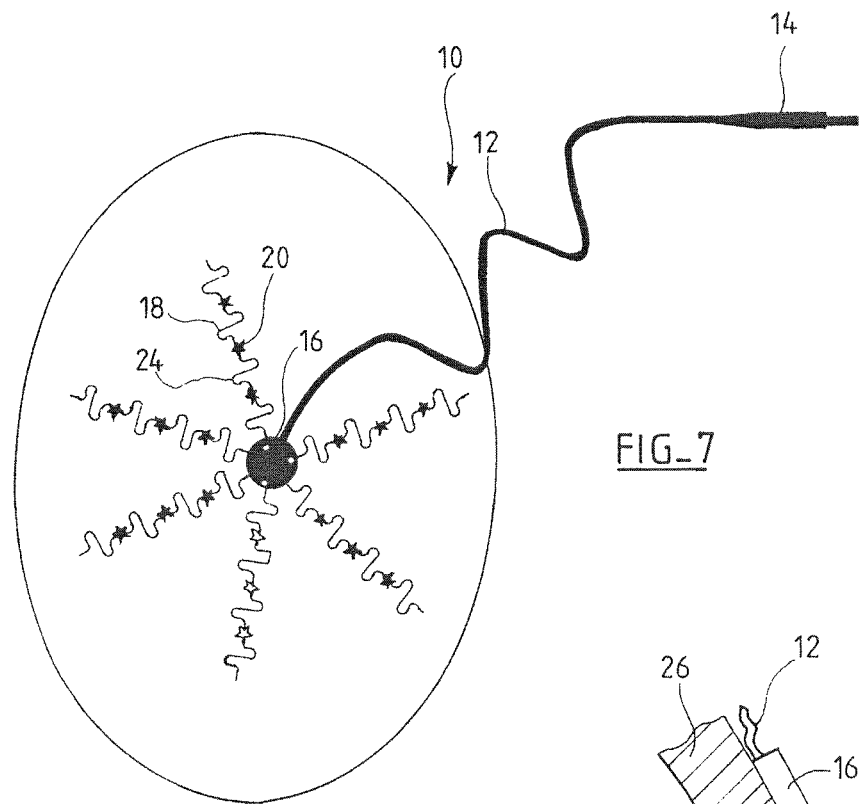
FIG_7
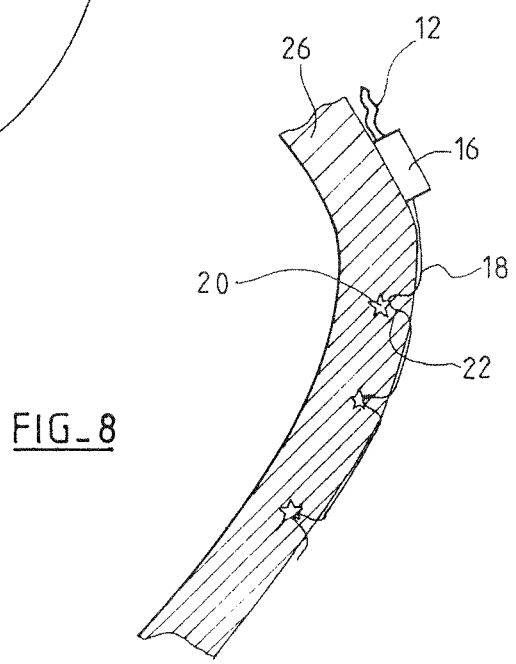
FIG_8

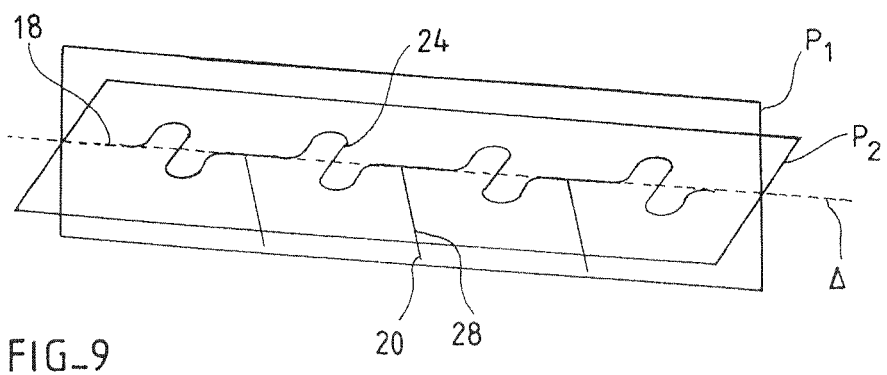
FIG_9
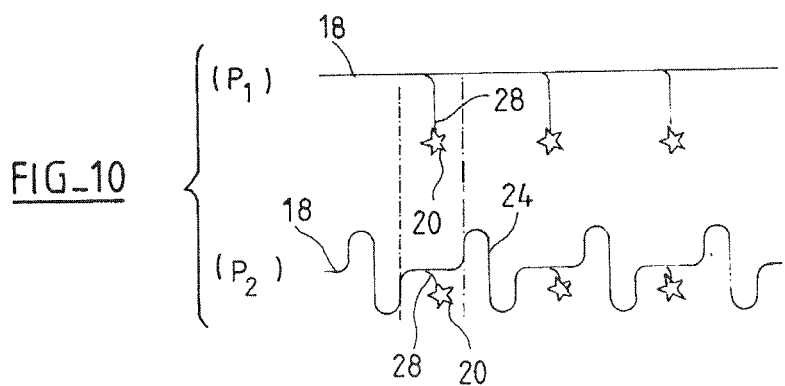
FIG_10
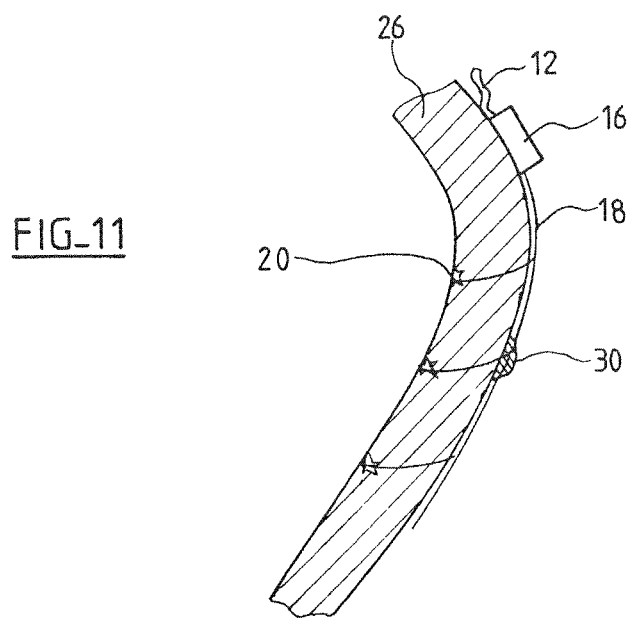
FIG_11

MULTIZONE EPICARDIAL PACING LEAD

RELATED APPLICATIONS

The present application claims the priority date benefit of French Patent Application No. 11/58882 entitled "Multizone Epicardial Pacing Lead" and filed Sep. 30, 2011.

FIELD OF THE INVENTION

The present Invention relates to "active implantable medical devices" as defined by the Jun. 20, 1990 90/395/CEE directive of the European Community Council, which includes devices that continuously monitor a patient's cardiac rhythm and deliver to the heart if and as needed electrical pulses for stimulation (pacing), cardiac resynchronization, cardioversion and/or defibrillation in response to a rhythm disorder detected by the device, and more particularly to "epicardial" leads that are directly fixed on the outer wall of the heart, as contrasted with "endocardial" leads which are inserted in a cavity of the heart where they are introduced via the venous system, and "coronary" leads implanted in the heart coronary network.

BACKGROUND

The epicardial leads may be prescribed for the stimulation of the left ventricle, as an alternative to pacing leads implanted via the coronary sinus, which require a delicate approach for their implantation and are not without various drawbacks.

Nevertheless, unlike endocardial leads introduced via the venous network (see for example U.S. Pat. Publication No. 2009/0157136 A1), the implantation of an epicardial lead constitutes a very invasive operation, usually requiring general anaesthesia and the use of surgical techniques. It is indeed necessary that a chest surgeon incises the thorax so as to provide access to the pericardial sac (the pericardium being the fibro-serous envelope that surrounds the heart) and the myocardium itself, in order to fix the lead on the external wall of the latter, by suturing or by screwing.

For this reason, the implantation of an epicardial lead, though representing a known technique, is often seen as a back-up solution in case of failure of implantation of a lead through the coronary sinus. Moreover, an epicardial lead often provides poor results, especially with respect to electrical performance.

Several types of epicardial leads have been proposed, but all have serious enough drawbacks. A first type of lead uses an electrode pressed against the wall of the epicardium, wherein it is supported by suturing. These leads are very stable, but require broad access to allow the suture by the surgeon, and the possible implantation zone is very limited, as it is restricted to the vicinity of the chest incision.

A variant of this type of lead is a lead body that is divided into two distinct branches, each branch having a distal end supporting a pacing electrode to be sutured on the cardiac wall. This support is provided by an absorbable suture terminated with a needle: during the procedure, after suturing the electrode to its support on the cardiac wall, the surgeon buries the absorbable suture using the needle, which needle is subsequently removed by cutting the suture. This permanent traction effort provides excellent contact of the electrode, positively biased against the heart wall. The presence of two separate electrodes also allows application of a bipolar stimulation, over a somewhat wider surface area.

Another type of lead proposed is equipped with an anchoring helical screw for screwing in the myocardium wall. Screwing can be performed directly, but the work area is then limited in the same way as a sutured lead. It can also be performed using a special insertion tool having an articulated head on which the lead is mounted, but the area of possible implantation, although broader, is nevertheless limited by the rigidity and the large diameter of the support tube of the instrument that the surgeon must manipulate in the curved pericardial space.

Moreover, from the mechanical point of view, the screws of current leads are very generously sized, due to the mechanical stresses exerted on the screw during implantation, arising from the high amplitudes of displacements and the radial tractions that are exerted. These generously sized screws are relatively traumatic to the tissues, with possible creation of local fibrosis reactions.

One disadvantage which is common to all these leads, besides the highly invasive surgery, is their relatively poor electrical performances, particularly because of the large size of the sutured electrode (which should ensure a satisfactory contact with the heart wall) or because of the large dimensions of the screw (needed to withstand implantation constraints). But a large electrode does not provide a satisfactory current density, which is detrimental to the stimulation efficiency.

In addition, the stimulation is punctual (only one stimulation site), with two drawbacks:
   A less effective stimulation compared to a multisite configuration, and
   The risk that the chosen site is not the most effective, or that because of cardiac remodeling, the site originally chosen over time become less effective. In this regard, given the invasive nature of the operation, it is not a realistic option to consider further surgery on the patient to try to improve the situation by seeking a possible alternative site that would be more effective than the originally chosen site.

A final drawback of existing epicardial leads, particularly for screw leads, is that it is almost impossible to extract them once they are implanted.

For all these reasons, the use of epicardial leads remains undeveloped, and these leads are generally used as a last resort when other techniques are not feasible.

The U.S. Pat. Publication No. 2007/0043412 A1 proposes a device implementing multiple electrodes (of a conventional type) located in different parts of the epicardium to form a network of electrodes. From an electrical point of view, each electrode is provided with its own connecting conductor, and the respective conductors are connected together to a common conductor connected at its other (proximal) end to the generator. The pacing pulses can thus be simultaneously spread to several electrodes at several points of the myocardium, corresponding to the points of implantation of the electrodes.

WO 2005/039690 A1 describes a different lead configuration, wherein two screw epicardial electrodes are implanted facing each of the two ventricles, each electrode being connected to the generator by its own conductor.

With these devices, since the electrodes used are of a conventional type (typically, screw electrodes), the problems mentioned above related to the nature of the electrodes remain, including: difficulty of implantation with the use of complex instruments particularly for in situ screwing after the implantation position is reached; need of a highly invasive intervention, which is traumatic for tissues with possible creation of a local fibrosis reaction of large sized screws because of mechanical constraints; poor electrical performances because of the large size of the electrode, which does not provide a satisfactory current density, to the detriment of the stimulation effectiveness.

OBJECT AND SUMMARY

It is, therefore, an object of the present invention to propose an epicardial lead having multiple stimulation points which is simple in construction (and therefore inexpensive to manufacture and with high reliability), and, above all, can also be implemented by operative techniques usually practiced by surgeons.

The present invention is directed to an epicardial pacing lead whose active part:
  guarantees an excellent and sustainable electrical contact with the tissues to stimulate; and
  improves the stimulation efficiency by multiplying or expanding the stimulation area, allowing (unlike traditional leads) simultaneous stimulation of several regions of the epicardium.

In this latter regard, it has been found with cardiac resynchronization therapy (CRT) devices that using multiple stimulation points on the left ventricle is a factor that substantially improves the quality of CRT.

Essentially, the solution of the present invention is to distribute on the surface of the heart muscle, or therein, an array of micro-electrodes that are in turn carried by a plurality of microcables.

These microcables are very flexible and extend outwardly from, i.e., radiate from a common distributor housing or hub, mounted at the end of an epicardial lead body, ensuring the distribution of current to the various microcables, with the possibility of bipolar pacing and/or of multiplexing of the different microcables. The distributor housing preferably has its own means for attachment to the heart wall (e.g., a suture or screw), and is itself devoid of any electrodes.

Broadly, the present invention is directed to an epicardial stimulation lead including, as known in the prior art, in particular from U.S. Pat. Publication No. 2007/0043412 A1 referenced above: a lead body made of a sheath of deformable material, enclosing at least one connection conductor; a proximal end including a connector for coupling the epicardial lead to a generator of an active implantable medical device; a distal end including a means for anchoring the epicardial lead to a wall of the epicardium and an active part comprising a plurality of stimulation electrodes, directly coming in contact with, or into, the wall of the epicardium; a distributor housing, placed at or near the distal end of the lead body, and a network of electrically insulated flexible conductors radiating from the distributor housing and extending between a proximal end connected to the distributor housing and a remote and free distal end, the proximal end being electrically connected at or via the distributor housing to an appropriate connection conductor of the lead body.

Preferably, the flexible conductors are microcable elements having a diameter of at most 2 French (0.66 mm). Each microcable more preferably comprises at least one denuded area, and each of these denuded areas forms one of the stimulation electrodes, such that the stimulation electrodes formed by denuded areas on the same microcable are electrically connected together. Each microcable further comprises at least one transverse elongate member extending at an angle to the main direction of the microcable, for penetrating into the wall of the epicardium.

In one embodiment, at least one transverse elongated member is a burying loop formed by a curvature of the microcable or a free extension formed on a bypass of the microcable.

In one embodiment, a radially distal end of said at least one transverse elongate member includes one of said denuded areas, so as to allow the electrode to be buried in the epicardium tissue—below the surface—to provide an in depth stimulation of the epicardium.

In one embodiment, each microcable comprises a succession of elongated portions extending along the main direction of the microcable, separated by compliance loops extending in a direction transverse to the microcable and providing the microcable flexibility and extensibility in the longitudinal direction.

In one embodiment, denuded areas of each microcable are formed at one radially distal end of the compliance loops, so as to allow a stimulation of the epicardium surface.

In one embodiment, the compliance loops and the transverse elongate elements extend in different respective planes forming an angle between them.

In one embodiment, the length of each microcable, in the deployed state, is between 5 and 80 mm.

In one embodiment, the distributor housing bears the anchoring means to a wall of the epicardium.

In one embodiment, the total exposed surface of the denuded areas of each microcable is at most 10 mm$^2$.

In one embodiment, the length in the longitudinal direction of each denuded area of each microcable is at most 10 mm.

In one embodiment, the lead body encloses a connection conductor comprising a plurality of separate connection conductors, and the lead comprises a corresponding plurality of microcables electrically isolated from each other and respectively connected to the plurality of connection conductors, so as to allow a bipolar or multipolar stimulation between denuded areas of different respective microcables.

In a preferred embodiment, the lead comprises a corresponding plurality of microcables electrically isolated from each other, and the distributor housing comprises a controlled switch means between on the one hand, a microcable selected from a number of the plurality of microcables and, on the other hand, a common connection conductor of the lead body, so as to allow selection from among the denuded areas from different respective microcables.

In one embodiment, the microcable is formed of a plurality of wires twisted together, wherein at least some of the wires incorporate a core of a radio-opaque material such as platinum-iridium or tantalum wrapped in a mechanically durable sheath of a material such as nitinol (NiTi) or stainless steel (or vice versa).

Preferably, the microcable comprises a multiwire structure coated by an insulating material, for example, parylene or a sheath of PET or PMMA, wherein the denuded areas are formed by ablation, leaving openings in the insulating layer along the microcable.

In one embodiment, the distal end of each microcable has a curved needle for stitching and burying of the microcable during implantation of the lead, this needle being subsequently separated from the microcable by cutting (e.g., an absorbable suture may be provided between the needle and the end of the microcable for this purpose).

DRAWINGS

Further features, characteristics, and advantages of the present invention will become apparent to a person of ordinary skill in the art from the following detailed description of preferred embodiments of the present invention, made with reference to the annexed drawings, in which:

FIG. 1 schematically illustrates an epicardial lead according to a first preferred embodiment of the present invention;

FIG. 2 schematically illustrates an epicardial lead according to a second embodiment of the present invention wherein each microcable has a plurality of stimulation electrodes;

FIG. 3 schematically illustrates an epicardial lead according to a third embodiment of the present invention implementing a multiplexing system between the different microcables of the lead;

FIG. 4 illustrates a perspective view of a first representative configuration for a microcable for an epicardial lead of the present invention;

FIG. 5 illustrates the microcable of FIG. 4, seen in projection in two orthogonal planes P1 and P2;

FIG. 6 illustrates a variant of FIG. 5, with a different positioning of the stimulation electrodes;

FIG. 7 is a schematic plan view of an epicardial lead according to the present invention, implanted with a microcable configuration such as that illustrated in FIG. 5;

FIG. 8 is homologous to the epicardial lead of FIG. 7, in a cross-sectional view through the heart wall;

FIG. 9 illustrates a perspective view of a second possible configuration of a microcable for a lead of the present invention;

FIG. 10 illustrates the microcable of FIG. 9, seen in projection in two orthogonal planes P1 and P2; and FIG. 11 is a schematic view, in cross section, through the heart wall, of an epicardial lead according to the present invention, implanted with the microcable configuration of FIG. 9.

DETAILED DESCRIPTION

With reference to the drawing FIGS. 1-10, several exemplary embodiments of an epicardial lead in accordance with the present invention will now be described.

The epicardial lead 10 according to the present invention essentially comprises a lead body 12 terminated at its proximal end by a connector 14 of conventional type (IS-1 or IS-4).

At its distal end, lead body 12 has a distributor housing or hub 16 provided with anchoring means of a known type (e.g. a suture or a screw), but which is not stimulating: indeed, the present invention does not expect or require distributor housing 16 to carry a stimulation electrode. Distributor housing 16 preferably includes a perforated foil collar to strengthen the anchoring by development of fibrosis. Distributor housing 16 may, for example, have a flattened cylindrical shape, with a typical diameter of 6 mm and a height of 4 mm.

In one embodiment, a plurality of microcables 18 is connected to distributor housing 16 by their proximal ends, their other distal ends being free (optionally already provided with a needle attached for the surgeon to use, who removes it once the implantation is performed). Distributor housing 16 includes typically six to eight microcables 18, but this number is given only as an example and is not intended to be limiting in any way. The length of each microcable 18, in the deployed state, is typically between 5 and 80 mm.

Distributor housing 16 ensures the physical connection of each electrical microcable 18 with a corresponding internal conductor of lead body 12, this conductor extending to connector 14.

The term "microcable" should be understood to refer to a very small diameter cable, of at most two French (0.66 mm), preferably about 1 French (0.33 mm). Each microcable is formed of an electrically isolated metallic conductor, except for at least one denuded area 20 or "window", forming a corresponding stimulation electrode (represented by a star in the Figures).

In the embodiment illustrated in FIG. 1, each microcable 18 includes one denuded area 20, 20' forming an electrode (hereinafter, the terms "denuded area", "electrode" and "window" are interchangeably used).

A first number of microcables 18 carry electrodes 20 and are connected together in distributor housing 16 to a first conductor of lead body 12, and a second number of microcables 18 carrying electrodes 20' connected together and to a second conductor of lead body 12, the second conductor being different from the first conductor. It is thus possible to apply bipolar pacing between, on one hand, electrodes 20 (schematically shown by white stars) and electrodes 20' (schematically shown by black stars).

With reference to FIG. 2, an embodiment is shown in which each microcable 18 carries a plurality of electrodes, for example, two electrodes 20 or two electrodes 20', which thus expands the stimulation area along a same microcable.

With reference to FIG. 3, a third embodiment is illustrated in which microcables 18 respectively include electrodes 20, 20', 20'', 20''' . . . and wherein each microcable 18 is connected to the input of a multiplexing module having a switch incorporated in distributor housing 16. An appropriate command sent to the multiplexing module housing is used to select at will via the switch the one or the other set of electrodes 20, 20', 20'', 20'''' . . . to test the possible stimulation sites and choose the one or ones providing the best results from a physiological standpoint. The multiplexing system can be, for example, that described in EP 1938861 A1 (and its counterpart: U.S. Pat. Publication No. 2008/0177343) and EP 2082684 A1 (and its counterpart: U.S. Pat. Publication No. 2009/0192572) (both assigned to Sorin CRM S.A.S., previously known as ELA Medical), which are hereby incorporated herein by reference. Such a multiplexing module allows in particular to implement the concept of "electronic repositioning" to direct or redirect the electric field between different electrodes by selecting, among the various possible configurations, those providing the best efficiency from the electrical and hemodynamic points of view. This technology also helps to manage the behavior of hemodynamic changes (reverse remodeling), simply by reprogramming the generator via telemetry through the skin, without the need for further surgical intervention.

In a preferred embodiment, to increase the stimulation area a variant of the present invention is to provide, for example, four independent microcables 18 or groups of microcables 18 each connected to four separate conductors within lead body 12. Connector 14 is then implemented as an appropriate connector, for example, of the IS-4 type, thus benefiting from four independent stimulation areas.

In all cases, denuded areas 20 of each microcable 18 form a succession of individual electrodes, together constituting a set of electrodes connected in series. This allows multiple points of contact with the heart wall and thus ensures a multizone distribution of the stimulation energy at several points in the epicardium and thus the left ventricle.

Preferably, the individual surface area of each electrode is at most 1 $mm^2$, which allows disposing several electrodes on microcable 18 without exceeding a combined total area of 10 $mm^2$. Due to the low cumulative surface area, the benefits of a "high current density" lead is achieved, with both more efficient physiological stimulation and reduced energy consumption. Advantageously, this is achieved maximizing the likelihood of physical, therefore electrical, contact between the electrodes and excitable tissue, due to the multiplication of these electrodes.

Regarding microcable 18 used in these various embodiments, the core of it is advantageously made of nitinol (NiTi alloy) or of MP35N-LT (35% Ni, 35% Co, 20% Cr and 10% Mo stainless steel), materials whose main advantage is their extreme endurance and fatigue resistance, with a coating of platinum-iridium. The result is native corrosion resistance at the electrodes, while ensuring fatigue resistance, which are imperatively required.

More preferably, the structure of microcable 18 is advantageously a multiwire structure in which each wire strand is preferably consisting of a core of platinum-iridium coated by a thickness of nitinol or MP35N-LT—or vice versa, so as to optimize response to the requirements of both corrosion and fatigue resistance. The wire strands can then be coated with a thin layer of parylene (for example, of C type). In this case, more or less complex windows are arranged along the microcable, for example by plasma ablation, to form electrodes 20. To improve the electrical performance, these denuded areas can further be coated, for example, with titanium nitride. Alternatively, the wire strands can be enveloped in a polyurethane tube interrupted (i.e., containing apertures) at the locations of electrodes 20; or one or more layers made of tubes made of PET (polyethylene terephthalate), fluoropolymer, PMMA (methyl polymethacrylate), PEEK (polyetheretherketone), polyimide or other suitable similar material.

Such a microcable structure, without any internal lumen and with several microwires braided together, is both enduring (against cardiac movements) and resisting to stress in particular during the implantation.

Another advantage of this solution, particularly significant, is due to the highly flexible and floating (floppy) property of the microcable, which provides excellent atraumaticity. In chronic implantation, such a microcable is very non traumatic to the tissues and thus preserves the cells in the immediate vicinity of the electrodes: one can therefore expect good electrical performance including in the long term, unlike the traditional epicardial leads, which are far more traumatic.

These types of braided microcables are available, for example, from Fort Wayne Metals Inc., Fort Wayne, Ind., USA, and are used in the medical field in particular for the production of defibrillation conductors—but having a different arrangement of materials: in these known applications the structure is a multiwire structure in which each wire includes a core of silver (to improve conductivity) coated by a thickness of stainless steel; these microstructures, isolated or not, are then incorporated into a multi-lumen lead body of classic construction.

Alternatively, it is nevertheless possible to have a platinum-iridium wire in the center of a 1×7-type multiwire structure, the more fragile wire being then embraced and protected by the more durable outer wires.

Finally, the platinum-iridium material can be replaced by any radio-opaque material such as tantalum.

Various possible geometric conformations of microcables 18 (preformed at manufacturing), with reference to FIGS. 4-11, will now be discussed.

In FIGS. 4 and 5, a first representative configuration is illustrated, wherein microcable 18 comprises a series of alternating corrugated portions 22, 24 with one or more transverse elongate members 22 extending in a first plane P1 and compliance loops 24 extending in a second plane P2 orthogonal to the plane P1, the intersection of these two planes P1 and P2 coinciding with the main direction Δ (longitudinal direction) of microcable 18.

Transverse elongate members 22 are landfill loops designed to make a penetration in the thickness of the epicardium, with the locally denuded areas 20 forming the stimulation electrodes, which are located on top of landfill loops 22.

Compliance loops 24, for example, formed as two half-periods of a sinusoid or of a similar shape, can prevent the transmission of cyclic stresses, resulting from the beating of the heart, to the stimulating areas formed by the electrodes 20 on top of landfill loops 22.

Note that the simplicity of the structure—isolated microcable with occasionally denuded areas forming the electrodes—allows without difficulty having an electrode on top of a (preshaped) ripple (corrugation) of the microcable, which would be much more difficult with conventional structures, for which it is considered that the areas of maximum curvature a priori are the most stressed ones, which leads to avoid locating the electrodes there.

Furthermore, placing denuded areas 20 at the top of the landfill loops 22 offers the possibility of employing sector electrodes. In this regard, in cross-sectional view, the denuded areas do not span around the entire periphery of microcable 18, but rather only span over an angular sector located on the side of the outer face of the curvature, that is to say the side facing the tissues with which they come into contact. It is thus possible to keep isolated much of the angular sector, which further limits the stimulating surfaces, resulting in the direct benefits outlined above in terms of increase of the current density.

The use of a buried electrode corresponding to the configuration of FIGS. 4, 5 and 8 allows in deep stimulation and reduces the risk of phrenic nerve stimulation, and the deep stimulation that it provides ensure better efficiency from the electrical and hemodynamic point of view.

Alternatively, it is possible to provide a different configuration, such as that illustrated in FIG. 6, wherein the electrodes 20 are arranged at the top of the compliance loops 24. Landfill loops 22 are then only used as anchors of the microcable to the heart wall. With this second configuration, the surface in which the compliance loops 24 extend is preferably a curved surface S2 (FIG. 4) instead of a plane P2, with a curvature directed towards the wall (that is to say in the direction of landfill loops 22). This allows forcing the mechanical contact of electrodes 20 with the muscle surface, due to the vertical spring effect of compliance loop 24, since the curvature of surface S2 is, in the free state, greater than that of the heart muscle.

With, in this method, a surface contact with the electrode instead of a buried electrode, the trauma suffered by the tissues is reduced, which increases the electrical performance. To reduce the risk of phrenic nerve stimulation, it is possible to sectorize the surface of stimulation electrodes 20 located at the top of compliance loops 24, that is to say the side facing the tissues with which they come into contact. It is thus possible to keep isolated much of the angular sector, which further limits the stimulating surfaces, resulting in the direct benefits outlined above in terms of increasing the current density.

FIGS. 7 and 8 are schematic views, respectively a plan view and a cross section view through the heart wall 26, of an epicardial lead according to the present invention with a microcable configuration such as that illustrated in FIG. 5, in an implanted situation.

The implantation of the lead according to the invention begins with the attachment of the distribution housing 16 to the heart wall.

The next step is to successively implant the various microcables on the heart wall, with burial of loop or loops 22 to ensure the continued position of the microcable. These loops 22, carrying (or not) the stimulation electrodes, may be buried in the muscle by a series of regularly spaced punctures.

The end of the microcable is equipped for this purpose, as explained above, with a curved needle, preferably factory fitted, to bite/bury the microcable at regular intervals, the needle being cut off after burial. The cut end of the microcable is then isolated by a deposit of biocompatible glue. To minimize the risk of creating an additional electrode at the location of the cut, it is possible to insert an absorbable suture between the needle and the end of microcable, the cut separating the needle being then performed on the absorbable suture.

It should be understood that the particular configuration of the lead of the invention is particularly well suited to an intervention by robotic microsurgical techniques, taking advantage of the remarkable capabilities of this technology to automatically operate "microsutures" controlled at a distance by the surgeon.

FIGS. 9, 10 and 11 are counterparts of FIGS. 4, 5 and 8, respectively, for a variant of the microcable in which the one or more transverse elongated elements, instead of being landfill loops, are free extensions 28 substantially straight, bearing at their free end stimulation electrode 20. These extensions 28 are connected at their other end to microcable 18 running on the surface of the heart muscle (this microcable 18 being of course provided with compliance loops 24 to prevent the transmission of stresses between the free extensions 28).

For implantation, each free extension 28 can be previously housed inside a puncture breakable micro-needle, to achieve the burial of the stimulating free extension 28 by insertion of the needle and subsequent removal of it (thanks to its breakability) once the landfill is made.

This microcable configuration delivers a deep stimulation of the myocardium, close to endocardial stimulation.

After surgery, the epicardial emergence of the free end is fixed to the wall by a known attachment method such as suture or deposit of adhesive point 30 of a biocompatible surgical adhesive such as BioGlue (registered trademark) available from Cryolife, Inc. (http://www.cryolife.com/products/bio-glue-surgical-adhesive).

One skilled in the art will appreciate that the present invention can be practiced by embodiments other than those described herein, which are provided for purposes of explanation, and not of limitation.

The invention claimed is:

1. An epicardial stimulation lead, comprising:
a lead body having a proximal end, a distal end, at least one connecting conductor and a sheath made of a deformable material, said sheath enclosing said at least one connecting conductor, the proximal end having a connector for coupling said at least one connecting conductor to a generator of an active implantable medical device,
a distributor housing disposed at the distal end of said lead body;
means for anchoring the distal end of the lead body to a patient's epicardium wall; and
an active part comprising a plurality of electrically insulated flexible microcable conductors having a proximal end, a distal end, and an insulating coating, the proximal ends being coupled to the distributor housing, the distal ends being free and remote from the distributor housing, said microcables being electrically connectable via the distributor housing to a connection conductor of the lead body, wherein:

each microcable has a main direction extending from said distributor housing and a diameter of at most equal to 2 French (0.66 mm);
each microcable comprises at least one denuded area in said insulating coating forming a stimulation electrode adapted to contact or penetrate an epicardium wall, the stimulation electrodes of a same microcable being electrically connected together, and
each microcable comprises at least one transverse elongated member
extending at an angle relative to the main direction of the microcable, and for penetrating into the wall of the epicardium, wherein said at least one elongated member is a transverse landfill loop formed by a curvature of the microcable.

2. The epicardial lead of claim 1, wherein a radially distal end of said at least one transverse elongated member carries one of said denuded areas to provide a buried stimulation electrode for in depth epicardium stimulation.

3. The epicardial lead of claim 1, wherein the length of each microcable, in a deployed state, is between 5 and 80 mm.

4. The epicardial lead of claim 1, wherein the distributor housing bears the anchoring means to an epicardium wall.

5. The epicardial lead of claim 1, wherein the total exposed surface of the denuded areas of the microcable is not more than 10 $mm^2$.

6. The epicardial lead of claim 1, wherein the longitudinal length of each denuded area of each microcable is at most 10 $mm^2$.

7. The epicardial lead of claim 1, wherein the lead body encloses a plurality of separate connecting conductors, and the lead comprises a corresponding plurality of microcables electrically isolated from each other and respectively connected to the connecting conductors, so as to allow a bipolar or multipolar stimulation between the denuded areas of different respective microcables.

8. The epicardial lead of claim 1, wherein the lead comprises a corresponding plurality of microcables electrically isolated from each other, and the distributor housing comprises a controlled switch between on the one hand, a microcable selected from a number of the plurality of microcables and, on the other hand, a common connecting conductor of the lead body, so as to allow selection among the denuded areas of different respective microcables.

9. The epicardial lead of claim 1, wherein the microcable is formed of a plurality of strands twisted together, in which at least some of the strands incorporate a core of radio-opaque material coated with a mechanically durable conductive material or vice versa, wherein the mechanically durable conductive material is one of NiTi or stainless steel.

10. The epicardial lead of claim 1, wherein the microcable comprises a multiwire structure coated with an insulating material, wherein the denuded areas are formed by leaving openings by removal of insulating material along the microcable.

11. The epicardial lead of claim 1, further comprising a curved needle attached at the distal end of the microcable for the stitching and the burying of the microcable during implantation of the lead, said needle being subsequently separatable from the microcable by cutting.

12. The epicardial lead of claim 11, further comprising an absorbable cuttable suture connecting the needle and the end of the microcable.

13. An epicardial stimulation lead, comprising:
a lead body having a proximal end, a distal end, at least one connecting conductor and a sheath made of a deformable material, said sheath enclosing said at least one connecting conductor, the proximal end having a connector for coupling said at least one connecting conductor to a generator of an active implantable medical device,
a distributor housing disposed at the distal end of said lead body;
means for anchoring the distal end of the lead body to a patient's epicardium wall; and
an active part comprising a plurality of electrically insulated flexible microcable conductors having a proximal end, a distal end, and an insulating coating, the proximal ends being coupled to the distributor housing, the distal ends being free and remote from the distributor housing, said microcables being electrically connectable via the distributor housing to a connection conductor of the lead body, wherein:
each microcable has a main direction extending from said distributor housing and a diameter of at most equal to 2 French (0.66 mm);
each microcable comprises at least one denuded area in said insulating coating forming a stimulation electrode adapted to contact or penetrate an epicardium wall, the stimulation electrodes of a same microcable being electrically connected together, and
each microcable comprises at least one transverse elongated member extending at an angle relative to the main direction of the microcable, and for penetrating into the wall of the epicardium, wherein said at least one transverse elongated member is a free extension formed on a bypass of the microcable.

14. The epicardial lead of claim 13, wherein a radially distal end of said at least one transverse elongated member carries one of said denuded areas to provide a buried stimulation electrode for in depth epicardium stimulation.

15. The epicardial lead of claim 13, wherein the distributor housing bears the anchoring means to an epicardium wall.

16. The epicardial lead of claim 13, wherein the total exposed surface of the denuded areas of the microcable is not more than 10 mm$^2$.

17. The epicardial lead of claim 13, wherein the lead body encloses a plurality of separate connecting conductors, and the lead comprises a corresponding plurality of microcables electrically isolated from each other and respectively connected to the connecting conductors, so as to allow a bipolar or multipolar stimulation between the denuded areas of different respective microcables.

18. The epicardial lead of claim 13, wherein the lead comprises a corresponding plurality of microcables electrically isolated from each other, and the distributor housing comprises a controlled switch between on the one hand, a microcable selected from a number of the plurality of microcables and, on the other hand, a common connecting conductor of the lead body, so as to allow selection among the denuded areas of different respective microcables.

19. The epicardial lead of claim 13, wherein the microcable is formed of a plurality of strands twisted together, in which at least some of the strands incorporate a core of radio-opaque material coated with a mechanically durable conductive material or vice versa, wherein the mechanically durable conductive material is one of NiTi or stainless steel.

20. The epicardial lead of claim 13, wherein the microcable comprises a multiwire structure coated with an insulating material, wherein the denuded areas are formed by leaving openings by removal of insulating material along the microcable.

21. The epicardial lead of claim 13, further comprising a curved needle attached at the distal end of the microcable for the stitching and the burying of the microcable during implantation of the lead, said needle being subsequently separatable from the microcable by cutting.

22. An epicardial stimulation lead, comprising:
a lead body having a proximal end, a distal end, at least one connecting conductor and a sheath made of a deformable material, said sheath enclosing said at least one connecting conductor, the proximal end having a connector for coupling said at least one connecting conductor to a generator of an active implantable medical device,
a distributor housing disposed at the distal end of said lead body;
means for anchoring the distal end of the lead body to a patient's epicardium wall; and
an active part comprising a plurality of electrically insulated flexible microcable conductors having a proximal end, a distal end, and an insulating coating, the proximal ends being coupled to the distributor housing, the distal ends being free and remote from the distributor housing, said microcables being electrically connectable via the distributor housing to a connection conductor of the lead body, wherein:
each microcable has a main direction extending from said distributor housing and a diameter of at most equal to 2 French (0.66 mm);
each microcable comprises at least one denuded area in said insulating coating forming a stimulation electrode adapted to contact or penetrate an epicardium wall, the stimulation electrodes of a same microcable being electrically connected together, and
each microcable comprises at least one transverse elongated member extending at an angle relative to the main direction of the microcable, and for penetrating into the wall of the epicardium, wherein each microcable comprises a succession of elongated portions extending along the main direction of the microcable, separated by compliance loops extending in a direction transverse to the microcable and providing the microcable flexibility and extensibility in the longitudinal direction.

23. The epicardial lead of claim 22, wherein the denuded areas of each microcable are formed at one radially distal end of the compliance loops to provide surface epicardium stimulation.

24. The epicardial lead of claim 22, wherein the compliance loops and the transverse elongate elements extend in different respective planes, forming an angle between them.

* * * * *